US005626628A

United States Patent [19]

Ganansia

[11] Patent Number: 5,626,628

[45] Date of Patent: May 6, 1997

[54] USES FOR AN ELECTRO-ANAESTHESIA APPARATUS

[76] Inventor: Michel Ganansia, 8, Allée des Pêcheurs, 91120 Palaiseau, France

[21] Appl. No.: 374,600

[22] PCT Filed: Jul. 23, 1993

[86] PCT No.: PCT/FR93/00759

§ 371 Date: Jan. 23, 1995

§ 102(e) Date: Jan. 23, 1995

[87] PCT Pub. No.: WO94/02200

PCT Pub. Date: Feb. 3, 1994

[30] Foreign Application Priority Data

Jul. 23, 1992 [FR] France ................. 92 09276

[51] Int. Cl.⁶ .................................. A61N 1/20
[52] U.S. Cl. ................................... 607/47
[58] Field of Search ................. 433/29, 32, 119; 607/1–3, 46, 47, 63, 115, 116, 118, 134

[56] References Cited

U.S. PATENT DOCUMENTS

| 566,103 | 8/1896 | Waite | 607/2 |
|---|---|---|---|
| 2,866,461 | 12/1958 | Suzuki | 607/47 |
| 3,955,583 | 5/1976 | Hörauf | 607/47 |
| 4,550,733 | 11/1985 | Liss et al. | 607/47 |
| 4,784,142 | 11/1988 | Liss et al. | 607/47 |
| 4,820,152 | 4/1989 | Warrin et al. | 433/119 |
| 5,236,358 | 8/1993 | Sieffert | 433/119 |

FOREIGN PATENT DOCUMENTS

| 0445742 | 9/1991 | European Pat. Off. . |
| 2659241 | 9/1991 | France . |

OTHER PUBLICATIONS

"Illustrated Dictionary of Denistry" 1982 by Stanley Jablonski.

*Primary Examiner*—William E. Kamm
*Assistant Examiner*—George R. Evanisko
*Attorney, Agent, or Firm*—Young & Thompson

[57] ABSTRACT

A novel use of an electronic medical electro-anaesthesia apparatus based on an adjustable DC power supply and electrodes which are interchangeable depending on the kind of operation, is disclosed. The apparatus comprises a housing (1) which an electronic device for regulating and controlling the DC power supply, and two electrodes of which one (2) is a patient-held member for gripping the housing while the other is any scaling instrument (15) used by the practitioner. The enamel of the teeth may be scaled with the instrument and the operation may be performed with full or partial desensitization. Another use of the apparatus relates to paradontic curetting.

3 Claims, 1 Drawing Sheet

5,626,628

USES FOR AN ELECTRO-ANAESTHESIA APPARATUS

BACKGROUND OF THE INVENTION

1. Field of the Invention

The present invention relates to an extension to the use of an electro-anaesthesia apparatus preferably employed in the domain of dental care.

2. Description of the Related Art

This electronic device is based on the use of D.C. currents and it has formed the subject matter of an earlier Patent Application by the Applicant, published under No. 2 659 241. The disclosure of FR 2 659 241 is incorporated herewith in its entirely. Schematically, it comprises a control housing and electrodes interchangeable depending on the mode of use chosen by the practitioner. This electronic device is shown in FIG. 1, in which the same reference numerals are used as in the FR 2, 659 241 application, for ease of reference.

One of the electrodes is constituted by the tool used during the operation (instruments, turbines), while the second electrode is none other than a member for gripping the housing, held by the patient. The two are consequently in simultaneous contact with two parts of the patient's body when the practitioner is carrying out his operation, and the electric circuit is closed for the duration of work of the tool in the mouth.

The source of direct current makes it possible to obtain currents adjustable in the microamp and milliamp ranges, whose uses are adapted to the various applications of the device. This latter comprises means for adjusting the intensity, for switching the polarities and/or scale, a means for visually monitoring the intensity of one or more electric signals, as well as electrically switchable outputs.

One of the major advantages of this apparatus is that it is easy to adapt it to the patient's threshold of sensitivity. In fact, if there is a domain where inequality particularly exists, it is in the sensation of pain felt by man. Certain people are virtually insensitive to stimuli considered to be painful by others, while others react to the least stimuli. This is particularly true concerning teeth. The fact that one is close to the nervous centres, which "manage" pain, is probably not irrelevant.

In the present case, the anaesthesic threshold may be rapidly adapted by modifying the intensity of the current, and even the current scale, depending on the case. The device lends itself well to this ease of adjustment, in view of its simplicity resulting from the fact that it is question only of a simple source of current, whose intensity may be modified by a knob located on the housing.

Up to the present time, practitioners employed this electro-anaesthesia device with their traditional tools of the odontological instruments, turbines, etc. . . type. The tool is then in contact with the dentine and the current is transmitted to the dentine via the metal electrode constituted by said tool, via the drill. It is therefore the tool itself which induces the anaesthesic effect.

This type of dental electro-anaesthesia proves satisfactory in nearly 90% of cases, and is explained by a hyperpolarization of the nervous fibers by the polarized current which blocks the nervous influx, vector of pain.

From the practitioner's point of view, in addition to the considerable versatility of use already mentioned, mention may also be made of the immediate anaesthesic effect reduced to the duration of the operation alone, the immediate and permanent control of the sensitivity, the total absence of toxicity, the absence of risk of allergy, etc. . . To this must be added the less purely scientific dimension of the patient's participation, who reacts to the stimuli felt. The therapy/patient binomial thus reconstituted, each participates in the operation as actor.

However, these advantages do not conceal the fact that the domain of application theoretically covered by this apparatus was up to the present time confined to certain applications which clearly follow from the generic name of the treatment: dentine electro-anaesthsia, as its name indicates, concerns only anaesthesic applications of operations on the dentine.

In other words, operations as painful as scaling of the teeth or paradontic curetting did not seem to be concerned by the advantages of the apparatus mentioned.

Several reasons were opposed to the increasing demand of practitioners attracted by the ease of use and the efficiency of the device and who would, of course, have wished to extend them to the field of scaling. In the first place, it appeared obvious that a device based on an electrical phenomenon of conduction of current would be inefficient for an operation concerning the enamel of the teeth, which, as is known, constitutes an excellent insulator. Here, the limitation follows from the characteristics of conductivity of the parts of the body treated.

In the second place, the very nature of the treatment, obtained by vibrations of a tip placed in contact with the enamel, seemed to be an obstacle. In fact, the vibrations may for example be produced thanks to a system of piezoelectric type supplied by an electric energy source leading to the production of ultrasonic mechanical vibrations with the aid of the piezoelectric crystal. In order to insulate the technical device, based on an electromechanical phenomenon, it was heretofore usual to envelop it in a plastified sheath constituting the handle of the tool. Consequently, there were no possible interferences between the internal electric phenomenon and the user.

In brief, a tool with plastic handle is traditionally used for scaling a tooth, while the apparatus forming the subject matter of the discussion, being an electrode, is necessarily metallic. The obstacle is that the tool is in that case the seat of two theoretically independent electrical phenomena, one electromechanical with the use of piezo-electricity, and the other purely electrical with the passage of the current in the tool, of which it is not known whether they interfere on one another, and even with the user.

These various reasons explain that, up to the present time, the invention forming the subject matter of patent application No. 2 659 241 had never been used for a scaling operation.

SUMMARY OF THE INVENTION

It is, therefore, an object of the present invention, to provide a novel use for the apparatus described in the Patent Application FR 2 659 241-A1, such as scaling of the enamel.

It is another object of the present invention to utilize the above-mentioned apparatus for the novel use of paradontic curetting.

It is a further object of the present invention to utilize the above-mentioned apparatus for the novel use of increasing the efficacity of anesthetics and of fixing the anaesthetic in the region of injection.

DESCRIPTION OF THE PREFERRED EMBODIMENT

Figure 1:
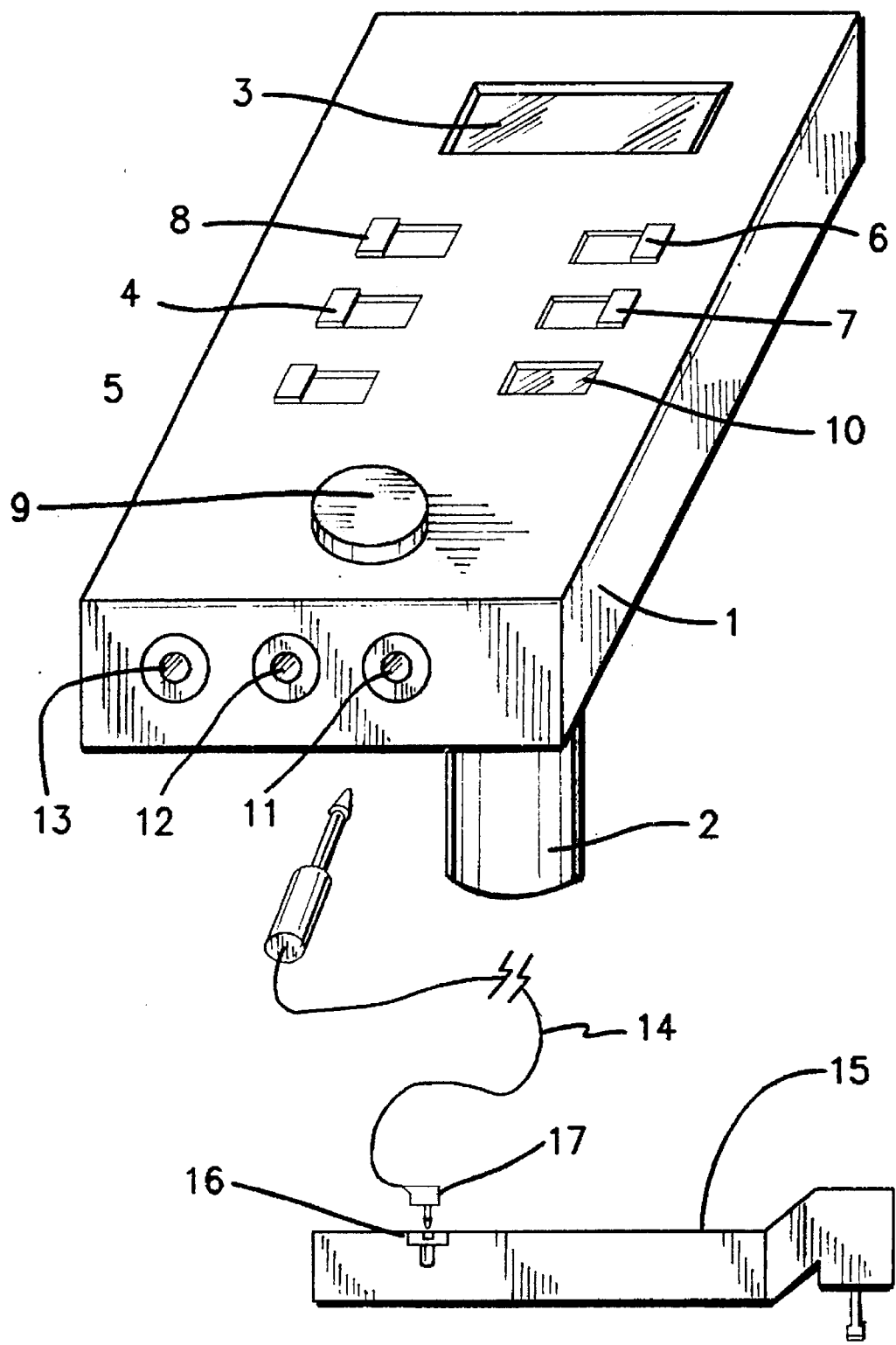
FIG. 1 is a diagram of the device disclosed in patent application FR 2 659 241-A1.

Despite the unfavourable prejudice explained above, further to the success encountered in its conventional applications, and in order to take into account the increasing demand of the specialists, tests have been made with a scaling tip.

These tests have shown that the use of the apparatus described in the Patent published under No. 2 659 241 in the domain of scaling is not only possible, but procures excellent results, despite the action of the tool on the enamel of the tooth instead of the dentine.

The surprizing experimental observation has for example been made that, contrary to all logic, the non-conductive nature of the dental enamel does not oppose the exercise of the anaesthesic effects of the device, for example on the well known pain provoked by any scaling instrument, and, on the contrary, provokes a reduction of the patient's sensitivity in the zone treated.

The pain generally provoked by the vibration of the ultra-sonic device in contact with the enamel may go as far as disappearing although said vibration is exactly the same, under the effect of the electro-anaesthesia simultaneously contributed by the electrode.

The invention therefore relates to a novel use of an electro-anaesthesia device furthermore known and described by Applicant, based on an adjustable D.C. source, conventionally used exclusively in contact with the dentine due to the presuppositions concerning the action of the D.C. current with a view to an action of scaling the nonconducting enamel. This takes place via any scaling instrument connected by a specific process to the electronic housing of the apparatus and serving as electro-anaesthesia electrode.

The efficacy of this novel use depends, of course, as for the other applications, on the threshold of sensitivity of the patient who may be brought to make the adjustments himself to raise the degree of anaesthesia if he feels pain. It makes it possible to arrive at a partial or total desensitization of the operation.

According to a use conceptually fairly close to scaling, the apparatus may also be used for paradontological care such as paradontic curetting.

In these cases, one adequate scale of micro-currents is included between 1 µA and 28 µA, and the other between 0.1 mA and 2.8 mA, depending on the patient's sensitivity. It should be noted that these intervals are different from the one which was used for more conventional dental applications relating to Applicant's. earlier Application.

According to another novel use of the Applicant's device, it was realized during tests that it potentializes the effects of traditional chemical anaesthetics injected in the patient's jaw.

In other words, the combined use of a conventional injected anaesthetic and of a tool/electrode allowing D.C. current to pass contributes to increasing the efficacy of said anaesthetic, on the one hand, and tends to fix it in the region of the injection. In addition, its time for "taking" is clearly reduced.

With one sole pack of anaesthetic, one can consequently anaesthetize several zones and treat several teeth in one session, when, up to the present, one hesitated doing so, due to the necessity of injecting in different places several doses each corresponding to the volume of a complete pack. For reasons of toxicity and comfort of the patient, it was, for most of the time, impossible to treat several teeth during the same session.

In that case, depending on the case and the application of the electrode, the currents chosen may be in the scale of the µA's or the mA's, with an electrode polarized for most of the time positively, although it is also possible to polarize it negatively.

By way of example, the conjuction of the effects of the device with those of an injected anaesthesic substance, such as articaine or lignocaine, makes it possible to reduce by ⅕ to ⅛ the quantity of this substance, in the buccal sectors concerned, with all the advantages resulting therefrom.

I claim:

1. Use of an electronic medical electro-anaesthesia apparatus based on an adjustable D.C. power source outputting a D.C. current, said apparatus comprising electrodes which are interchangeable depending on a kind of operation, said electrodes being electrically connected to said D.C. power source, said apparatus comprising a housing with electronic means for regulating and controlling the D.C. power source, said use comprising the steps of:

adjusting said D.C. current;

gripping, by a patient, of a housing member, said housing member being one of said electrodes;

applying said D.C. current to an enamel of teeth of said patient with a practitioner's scaling instrument; said scaling of said enamel of the teeth with the aid of said scaling instrument arriving at one of a total and partial desensitization of the teeth during a scaling operation, said scaling instrument being another of said electrodes.

2. Use of the apparatus according to claim 1, in which a magnitude of the D.C. current, in said adjusting step, is adjusted within a range between 1 µA and 28 µA, depending on a patient's sensitivity.

3. Use of the apparatus according to claim 1, in which a magnitude of the D.C. current, in said adjusting step, is adjusted within a range between 0.1 mA and 2.8 mA, depending on a patient's sensitivity.

* * * * *